(12) United States Patent
Bernstein

(10) Patent No.: US 11,213,530 B2
(45) Date of Patent: Jan. 4, 2022

(54) GALLIUM IN THE TREATMENT OF CORONAVIRUS DISEASE

(71) Applicant: Lawrence Richard Bernstein, Menlo Park, CA (US)

(72) Inventor: Lawrence Richard Bernstein, Menlo Park, CA (US)

(*) Notice: Subject to any disclaimer, the term of this patent is extended or adjusted under 35 U.S.C. 154(b) by 97 days.

(21) Appl. No.: 16/906,542

(22) Filed: Jun. 19, 2020

(65) Prior Publication Data

US 2021/0275544 A1   Sep. 9, 2021

Related U.S. Application Data

(60) Provisional application No. 62/985,552, filed on Mar. 5, 2020.

(51) Int. Cl.
| | | |
|---|---|---|
| *A61K 33/24* | (2019.01) | |
| *A61K 47/02* | (2006.01) | |
| *A61P 31/14* | (2006.01) | |
| *A61K 31/555* | (2006.01) | |
| *A61K 9/08* | (2006.01) | |
| *A61K 9/12* | (2006.01) | |
| *A61K 9/00* | (2006.01) | |

(52) U.S. Cl.
CPC .......... *A61K 31/555* (2013.01); *A61K 9/0053* (2013.01); *A61K 9/0078* (2013.01); *A61K 9/08* (2013.01); *A61K 9/12* (2013.01); *A61K 33/24* (2013.01)

(58) Field of Classification Search
USPC .......................................... 424/650; 514/769
See application file for complete search history.

(56) References Cited

PUBLICATIONS

Orege et al., Advances in Traditional Medicine May 2021, Ahead of Print CODEN: ATMDC2; ISSN: 2662-4060; https://doi.org/10.1007/s13596-021-00576-5; downloaded Nov. 15, 2021.*

* cited by examiner

*Primary Examiner* — Raymond J Henley, III

(57) ABSTRACT

Provided are compositions and methods to treat or prevent coronavirus disease, including Covid-19. The methods comprise the administration of pharmaceutically acceptable gallium compounds. A preferred method is the oral administration of gallium maltolate, and another preferred method is inhalation of an aerosolized solution of gallium maltolate into the bronchi and lungs. Also provided are methods to destroy or otherwise inactivate coronaviruses on or in the body of an individual, on any surface, in any liquid, or in any gas including air, by direct contact with a gallium compound or with gallium in solution as a liquid or vapor.

20 Claims, 1 Drawing Sheet

SARS-CoV-2 virus in Vero-E6 cells $EC_{50} = 14\ \mu M$

Gallium maltolate concentration ($\mu M$; $\log_{10}$)

GALLIUM IN THE TREATMENT OF CORONAVIRUS DISEASE

TECHNICAL FIELD

This invention pertains to the treatment of diseases caused by coronaviruses, including Covid-19. In particular, this invention pertains to the use of pharmaceutically acceptable gallium compounds, including gallium maltolate, gallium 8-quinolinolate, gallium nitrate, and gallium citrate, to treat and prevent diseases caused by coronaviruses. The invention further pertains to destroying or otherwise deactivating coronaviruses by direct contact with a gallium compound or gallium in solution.

BACKGROUND OF THE INVENTION

As used in herein, and according to standard terminology in the field of virology, a coronavirus is a type of single-stranded RNA virus that is a member of the Orthocoronavirinae subfamily, in the Coronaviridae family. Coronaviruses are known to infect mammals and birds. Human diseases caused by coronaviruses include several varieties of the common cold, Middle East Respiratory Syndrome (MERS), and Severe Acute Respiratory Syndrome (SARS), including diseases caused by SARS-CoV-1 (or SARS-CoV) and SARS-CoV-2 (Covid-19). Coronavirus diseases that affect non-human animals include feline infectious peritonitis, canine coronavirus disease, equine coronavirus disease, and porcine epidemic diarrhea CoV. Many other coronavirus diseases are known to exist in mammals and in birds, and it is likely that there are other diseases in humans and animals caused by coronaviruses, and that new coronavirus diseases will arise in the future.

No effective vaccines currently exist for any coronavirus disease. Current treatment for coronavirus diseases is primarily supportive. Existing compounds that may be used in treatment have only modest therapeutic efficacy at best.

There is thus a clear and urgent need for an effective treatment for many coronavirus diseases, including Covid-19, which is caused by the SARS-CoV-2 virus.

We here report that gallium compounds, particularly gallium maltolate, are especially potent agents against coronavirus infections, particularly Covid-19. Gallium compounds and gallium in solution are also effective at destroying or otherwise deactivating coronaviruses on contact. Gallium has demonstrated antiviral activity against coronaviruses, as well as anti-inflammatory activity.

SUMMARY OF THE INVENTION

Accordingly, it is a primary object of the invention to provide pharmaceutical compositions, methods, and drug delivery systems for treating or preventing coronavirus disease, including Covid-19, which is caused by the SARS-CoV-2 virus.

In a methodological embodiment of the invention, a method for treating or preventing coronavirus disease is provided that comprises administering to an individual a therapeutically or prophylactically effective amount of a pharmaceutically acceptable gallium compound.

In another methodological embodiment of the invention, a method is provided for destroying or otherwise deactivating coronaviruses on or in the body of an individual, or on any surface, or in any liquid, or in any gas including air, by direct contact with a gallium compound or with gallium in solution, as a liquid or vapor.

Additional objects, advantages, and novel features of the invention will be set forth in part in the description that follows, and in part will become apparent to those skilled in the art upon examination of the following, or may be learned by practice of the invention.

BRIEF DESCRIPTION OF THE DRAWING

FIG. 1 shows the in vitro inhibition of coronavirus SARS-CoV-2 replication by gallium maltolate at several concentrations.

DETAILED DESCRIPTION OF THE INVENTION

Before the present compositions, methods, and drug delivery systems of the invention are disclosed and described, it is to be understood that this invention is not limited to specific formulations, i.e., specific carrier materials or the like, to specific dosage regimens, or to specific drug delivery systems, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a gallium compound" includes mixtures of such compounds; reference to "a carrier" includes mixtures of two or more carriers; and the like.

The terms "patient", "individual", or "subject" are meant to include a human or a veterinary patient, individual, or subject. Veterinary patients, individuals, or subjects include non-human animals, particularly mammals and birds.

The terms "active agent," "drug," and "pharmacologically active agent" are used interchangeably herein to refer to a chemical material or compound that, when administered to an organism (human or animal, generally human) induces a desired pharmacologic effect, such as treatment of coronavirus disease.

The terms "to treat" and "treatment" as used herein encompass the usual meanings of these terms plus the usual meanings of the terms "to prevent" and "prevention". Thus, for example, "treatment" of coronavirus disease, as the term "treatment" is used herein, encompasses both prevention of coronavirus disease in a predisposed individual, such as an individual exposed to the disease or is in danger of being exposed to the disease, as well as treatment of coronavirus disease in an individual who has such a disease.

By the term "effective" amount of a drug is meant a sufficient amount of a compound to provide the desired effect and performance at a reasonable benefit/risk ratio attending any medical treatment.

This invention includes gallium compositions suitable for the administration of gallium, and devices and methods for using such compositions to treat coronavirus disease, including Covid-19.

The pharmaceutical compositions of the invention comprise a pharmaceutically acceptable gallium compound.

This invention involves the use of pharmaceutically acceptable gallium compounds to treat or prevent coronavirus disease, including those diseases caused by coronaviruses, such as Covid-19.

In one embodiment of the invention, a patient may first be screened for suitability for treatment by conducting a gallium scan (using a gallium radioisotope, such as $^{67}$Ga or $^{68}$Ga): if the gallium scan (or other means) shows that tissues infected by a coronavirus concentrate gallium, then the patient may be deemed particularly suitable for therapeutic treatment with gallium.

Any pharmaceutically acceptable gallium compound may be used therapeutically in this invention, by any medically acceptable route of administration. Gallium compounds usable in this invention include, without limitation, gallium nitrate, gallium sulfate, gallium citrate, gallium chloride, gallium complexes of 3-hydroxy-4-pyrones including gallium maltolate, gallium tartrate, gallium succinate, gallium gluconate, gallium palmitate, gallium 8-quinolinolate, gallium porphyrins including gallium(III) protoporphyrin IX, gallium transferrin, bis(2-acetylpyridine 4N-dimethylthiosemicarbazone)gallium (III)-gallium(III) tetrachloride, gallium pyridoxal isonicotinoyl hydrazone, a gallium(III) complex with 7-chloroquinoline thiosemicarbazone, gallium complexes of kenpaullone and its derivatives, and any other pharmaceutically acceptable gallium salts, organic salts, inorganic compounds, chelates, complexes, coordination compounds, and organometallic compounds. Gallium maltolate is a preferred gallium compound of the invention; this compound is described, for example, in U.S. Pat. No. 5,981,518 to Bernstein.

In one embodiment, the gallium compound is administered intravenously; for this purpose, gallium nitrate, gallium citrate, gallium palmitate, gallium porphyrins including gallium(III) protoporphyrin IX, gallium transferrin, bis(2-acetylpyridine 4N-dimethylthiosemicarbazone)gallium (III)-gallium(III) tetrachloride, a gallium(III) complex with 7-chloroquinoline thiosemicarbazone, pyridoxal isonicotinoyl hydrazone gallium(III), gallium maltolate, and gallium complexes of kenpaullone and its derivatives, in a suitable pharmaceutically acceptable liquid formulation, are preferred, with citrate-buffered gallium nitrate particularly preferred.

In a further embodiment, which is preferred, the gallium compound is administered orally. For this route of administration, preferred compounds are gallium maltolate, gallium 8-quinolinolate, gallium nitrate, gallium citrate, and gallium chloride; gallium maltolate is particularly preferred.

In another preferred embodiment, the gallium compound is administered by inhalation into the bronchi and/or lungs. The inhaled composition may be either a liquid solution or a dry powder. For this route of administration, gallium maltolate, gallium 8-quinolinolate, gallium citrate, and gallium nitrate are preferred compounds, with gallium maltolate being particularly preferred. As a non-limiting example of a composition suitable for inhalation, a 0.1% to 1% solution of gallium maltolate in sterile, distilled water is prepared, which may be administered as an aerosol via nebulization or using similar methods.

In other embodiments, the pharmaceutically acceptable gallium compound is administered topically, transdermally, per rectum, vaginally, buccally, subcutaneously, intramuscularly, peritoneally, into the ear, topical ocularly, intraocularly, by instillation into the bladder, by installation into the nasal passages, by installation into the paranasal sinuses, urethrally, sublingually, using depot formulations and/or devices, or by any other safe and effective route known in the art of drug delivery. For topical, transdermal, rectal, vaginal, buccal, otic, topical ocular, intraocular, bladder, urethral, nasal, paranasal sinus, or sublingual delivery, gallium maltolate, gallium 8-quinolinolate, gallium citrate, and gallium nitrate are preferred compounds, with gallium maltolate being particularly preferred. For subcutaneous, intramuscular, or peritoneal delivery, gallium nitrate, gallium citrate, gallium maltolate, and gallium 8-quinolinolate are preferred compounds, with citrate-buffered gallium nitrate being particularly preferred.

The gallium compositions of the invention may also be formulated using liposomes. Such formulations may be particularly advantageous for sustained release or delayed release compositions.

The gallium compound is administered in an amount effective to treat or prevent coronavirus disease, including Covid-19. Such amounts, when administered systemically, generally result in plasma gallium concentrations of about 1 to 10,000 ng/mL, preferably about 100 to 5,000 ng/mL. Treatment is generally continued for 1 to 60 days, with treatment periods of 5 to 15 days being typical.

As an example of oral administration, gallium maltolate may be administered orally at a dose of about 50 to 5,000 mg/day, preferably about 200 to 3,500 mg/day, and more preferably about 500 to 2,500 mg/day, together with a pharmaceutically acceptable carrier. The dose may be administered in a single dose once per day, which is preferable, or in divided doses two or more times per day. The dose may be administered as a tablet, capsule, liquid, or other form known in the art of oral drug delivery. Preferred formulations include those that contain maltol in an amount of 1-50% of the weight of the gallium maltolate, as a means to enhance gallium absorption. Also preferred are chewable tablets. Treatment is generally continued for 1 to 60 days, with treatment periods of 5 to 15 days being typical.

In the treatment of coronavirus disease, including Covid-19, a gallium compound, such as gallium maltolate, may be administered as part of a treatment regimen that includes other active agents, such as antiviral agents and/or anti-inflammatory agents.

When used to destroy or otherwise deactivate a coronavirus on or in the body of an individual, or on any surface, or in any liquid, or in any gas including air, a gallium compound or solution of a gallium compound is brought into direct contact with the location to be so disinfected. The gallium compound may be solid, liquid, or gaseous. A solid gallium compound may be in any form; in some embodiments of the invention it will be a powder or as nanoparticles, which may be aerosolized or nebulized. The gallium compound may also be in a solution or a suspension in a liquid; the liquid may be any suitable liquid, including, as examples, water, saline solution, alcohol, a phenolic liquid, an oily liquid, an emulsion, mixtures of these liquids, and so on. The liquid may, as examples, be aerosolized, nebulized, or vaporized.

The practice of the present invention may employ, unless otherwise indicated, conventional techniques of drug formulation, which are within the skill of the art. Such techniques are fully explained in the literature. See, for example, Remington: The Science and Practice of Pharmacy, $22^{nd}$ Edition (2012), as well as Goodman & Gilman's The Pharmacological Basis of Therapeutics, $12^{th}$ Edition (2010), and Ansel's Pharmaceutical Dosage Forms and Drug Delivery Systems, $9^{th}$ Edition (2010).

All patents, patent documents, and publications cited herein are hereby incorporated by reference in their entirety for their disclosure concerning any pertinent information not explicitly included herein.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains.

EXPERIMENTAL

The following example is put forth so as to provide those of ordinary skill in the art with a complete disclosure and description of how to make and use the compositions of the invention. Examples are intended as non-limiting examples of the invention. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric.

Example 1

In Vitro Activity of Gallium Maltolate on Coronavirus SARS-CoV-2

A Vero-E6 cell line was obtained from the American Type Culture Collection (ATCC) and maintained in minimum Eagle's medium (MEM) supplemented with 10% fetal bovine serum (FBS) at 37° C. in a humidified atmosphere containing 5% $CO_2$. The Vero-E6 cells were infected with SARS-CoV-2 (WIV04) at a multiplicity of infection (MOI) of 0.005. The infected cells were treated with gallium maltolate dissolved in sterile, distilled water, at concentrations ranging from 0.1 µM to 100 µM. At 24 hours after treatment, the viral RNA levels in the cell culture media were measured using quantitative real-time reverse-transcriptase polymerase chain reaction analysis (qRT-PCR).

As shown in FIG. 1, gallium maltolate showed pronounced, dose-dependent in vitro antiviral activity. The concentration that inhibited viral replication by 50% ($EC_{50}$) was about 14 µM.

I claim:

1. A method for treating a disease caused by a coronavirus in an individual afflicted with such a condition, comprising administering to the individual a therapeutically effective amount of a composition comprising a pharmaceutically acceptable gallium compound.

2. The method of claim 1, wherein the disease is Covid-19.

3. The method of claim 1, wherein the gallium compound is selected from the group consisting of gallium hydroxypyrones including gallium maltolate, gallium 8-quinolinolate, gallium citrate, gallium acetate, gallium tartrate, gallium gluconate, gallium nitrate, gallium oxide, gallium hydroxide, gallium oxide hydroxide, gallium chloride, gallium sulfate, gallium polyalcohols such as gallium xylitol, gallium palmitate, gallium succinate, gallium pyridinones, gallium porphyrins such as gallium protoporphyrin IX (PPIX), gallium pyridoxal isonicotinoyl hydrazone, gallium complexes of kenpaullone and its derivatives, and [bis(2-acetylpyridine 4N-dimethylthiosemicarbazone) gallium (III), gallium(III) tetrachloride].

4. The method of claim 3, wherein the gallium compound is gallium maltolate.

5. The method of claim 3, wherein the gallium compound is gallium 8-quinolinolate.

6. The method of claim 3, wherein the gallium compound is gallium nitrate.

7. The method of claim 3, wherein the gallium compound is gallium citrate.

8. A method for destroying or otherwise inactivating coronaviruses on or in the body of an individual, on any surface, in any liquid, or in any gas including the air, by direct contact with a gallium compound or with gallium in solution as a liquid or vapor.

9. The method of claim 8, wherein the coronavirus is SARS-CoV-2.

10. The method of claim 8, wherein the gallium compound is selected from the group consisting of gallium hydroxypyrones including gallium maltolate, gallium 8-quinolinolate, gallium citrate, gallium acetate, gallium tartrate, gallium gluconate, gallium nitrate, gallium oxide, gallium hydroxide, gallium oxide hydroxide, gallium chloride, gallium sulfate, gallium polyalcohols such as gallium xylitol, gallium palmitate, gallium succinate, gallium pyridinones, gallium porphyrins such as gallium protoporphyrin IX (PPIX), gallium pyridoxal isonicotinoyl hydrazone, gallium complexes of kenpaullone and its derivatives, and [bis(2-acetylpyridine 4N-dimethylthiosemicarbazone) gallium (III), gallium(III) tetrachloride].

11. The method of claim 8, wherein the gallium compound is gallium maltolate.

12. The method of claim 8, wherein the gallium compound is gallium nitrate.

13. The method of claim 8, wherein the gallium compound is gallium citrate.

14. The method of claim 8, wherein the gallium compound is gallium 8-quinolinolate.

15. The method of claim 8, wherein the gallium in solution is a solution that contains gallium hydroxypyrones including gallium maltolate, gallium 8-quinolinolate, gallium citrate, gallium acetate, gallium tartrate, gallium gluconate, gallium nitrate, gallium oxide, gallium hydroxide, gallium oxide hydroxide, gallium chloride, gallium sulfate, gallium polyalcohols such as gallium xylitol, gallium palmitate, gallium succinate, gallium pyridinones, gallium porphyrins such as gallium protoporphyrin IX (PPIX), gallium pyridoxal isonicotinoyl hydrazone, gallium complexes of kenpaullone and its derivatives, or [bis(2-acetylpyridine 4N-dimethylthiosemicarbazone) gallium(III), gallium(III) tetrachloride].

16. The method of claim 15, wherein the gallium in solution is a solution of gallium maltolate.

17. The method of claim 15, wherein the gallium in solution is a solution of gallium nitrate.

18. The method of claim 15, wherein the gallium in solution is a solution of gallium chloride.

19. The method of claim 15, wherein the gallium in solution is a solution of gallium citrate.

20. A method for treating Covid-19 in an individual afflicted with such condition, comprising administering to the individual a therapeutically effective amount of a composition comprising gallium maltolate.

* * * * *